United States Patent [19]
Cozean, Jr. et al.

[11] Patent Number: 5,873,883
[45] Date of Patent: Feb. 23, 1999

[54] HYDRAULIC CAPSULORHEXITOME

[76] Inventors: Charles H. Cozean, Jr., Rte. 2, Box 383D, Cape Girardeau, Cape County, Mo. 63701; Charles H. Cozean, III, 11930 Montana Ave. Apt. 304, Los Angeles, Calif. 90049

[21] Appl. No.: 591,761

[22] Filed: Jan. 25, 1996

[51] Int. Cl.$^6$ .................................................. A61B 17/32
[52] U.S. Cl. ............................................. 606/166; 606/167
[58] Field of Search ............................. 606/1, 107, 166, 606/167, 170; 604/22; 30/45, 301, 316

[56] References Cited

U.S. PATENT DOCUMENTS

| | | |
|---|---|---|
| 2,473,968 | 6/1949 | Paton . |
| 3,809,093 | 5/1974 | Abraham . |
| 4,020,847 | 5/1977 | Clark, III . |
| 4,188,952 | 2/1980 | Loschilov et al. . |
| 4,345,516 | 8/1982 | Sinclair . |
| 4,406,285 | 9/1983 | Villasenor et al. . |
| 4,425,115 | 1/1984 | Wuchinich . |
| 4,515,583 | 5/1985 | Sorich . |
| 4,672,965 | 6/1987 | Baum . |
| 4,706,669 | 11/1987 | Schlegel . |
| 4,708,138 | 11/1987 | Pazandak . |
| 4,739,761 | 4/1988 | Grandon . |
| 4,766,897 | 8/1988 | Smirmaul . |
| 4,844,060 | 7/1989 | Krumeich . |
| 4,846,833 | 7/1989 | Cumming . |
| 4,878,912 | 11/1989 | Castleman . |
| 4,911,161 | 3/1990 | Schechter . |
| 5,030,201 | 7/1991 | Palestrant . |
| 5,108,412 | 4/1992 | Krumeich et al. . |
| 5,254,082 | 10/1993 | Takase . |
| 5,261,923 | 11/1993 | Soares ..................................... 606/166 |
| 5,269,787 | 12/1993 | Cozean, Jr. et al. . |
| 5,312,330 | 5/1994 | Klopotek .................................. 606/166 |

FOREIGN PATENT DOCUMENTS

| | | |
|---|---|---|
| 2588751 | 4/1987 | France . |
| 0591498 | 1/1934 | Germany . |
| 2811869 | 9/1979 | Germany . |
| 0242673 | 2/1987 | Germany . |
| 4012882 | 10/1991 | Germany . |
| 0448013 | 10/1974 | U.S.S.R. . |
| 1388037 | 5/1986 | U.S.S.R. . |
| 1335282 | 9/1987 | U.S.S.R. . |
| 1431752 | 10/1988 | U.S.S.R. . |
| 1500292 | 8/1989 | U.S.S.R. . |
| 1526704 | 12/1989 | U.S.S.R. . |
| 1535541 | 1/1990 | U.S.S.R. . |
| 2247174 | 2/1992 | United Kingdom . |

OTHER PUBLICATIONS

"Anterior Capsultomy With Ultrasound Cystotome", by Antonio Mendez, M.D., American Intraocular Implant Society Journal, vol. 10, Summer 1984, pp. 363–364.

"Visitec Offers A Cytotome To Fit Your Capsulotomy Technique", Booth No. 215, AIOIS Meeting (date & other information unknown).

"Battery–Powered Unit Aids Anterial Capsulectomy", IOL & Ocular Surgery News, Jul. 15, 1984, p. 23.

"Intraocular Tissues Are Different. Shouldn't Your Cutters Be? Site TXR™ Cutters Are", Ophthamology Times, Jul. 15, 1984, p. 61.

Journal of Ocular Therapy & Surgery, The Journal For Practicing Ophthalmologist, vol. 3, No. 1, Jan.–Feb. 1984, pages unknown.

Primary Examiner—William Lewis
Attorney, Agent, or Firm—Harold E. Meier

[57] ABSTRACT

A surgical apparatus and method for incising an aperture in the anterior capsule of the human eye are disclosed. The apparatus or capsulorhexitome, comprises a hollow shaft, a concentric cutting member with a annular channel and orifice, and means for injecting a substantially incompressible fluid through the apparatus to incise a smooth, continuous, curvilinear aperture in the anterior capsule of the eye.

21 Claims, 3 Drawing Sheets

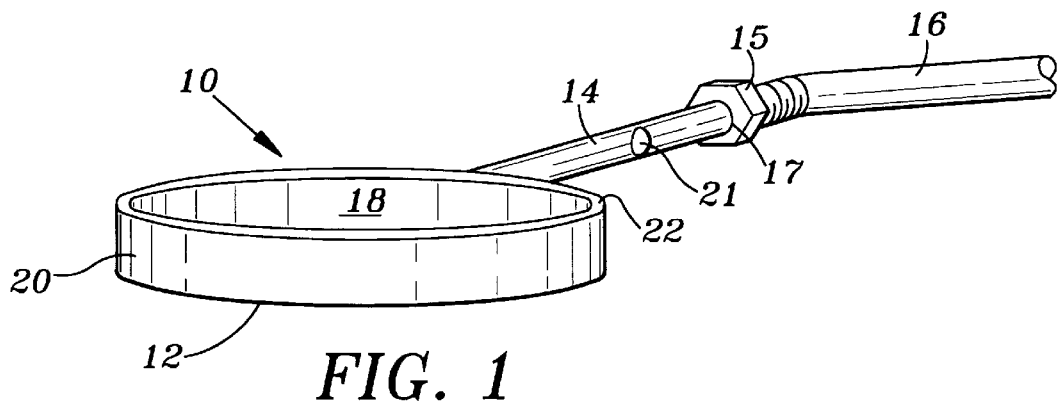
FIG. 1
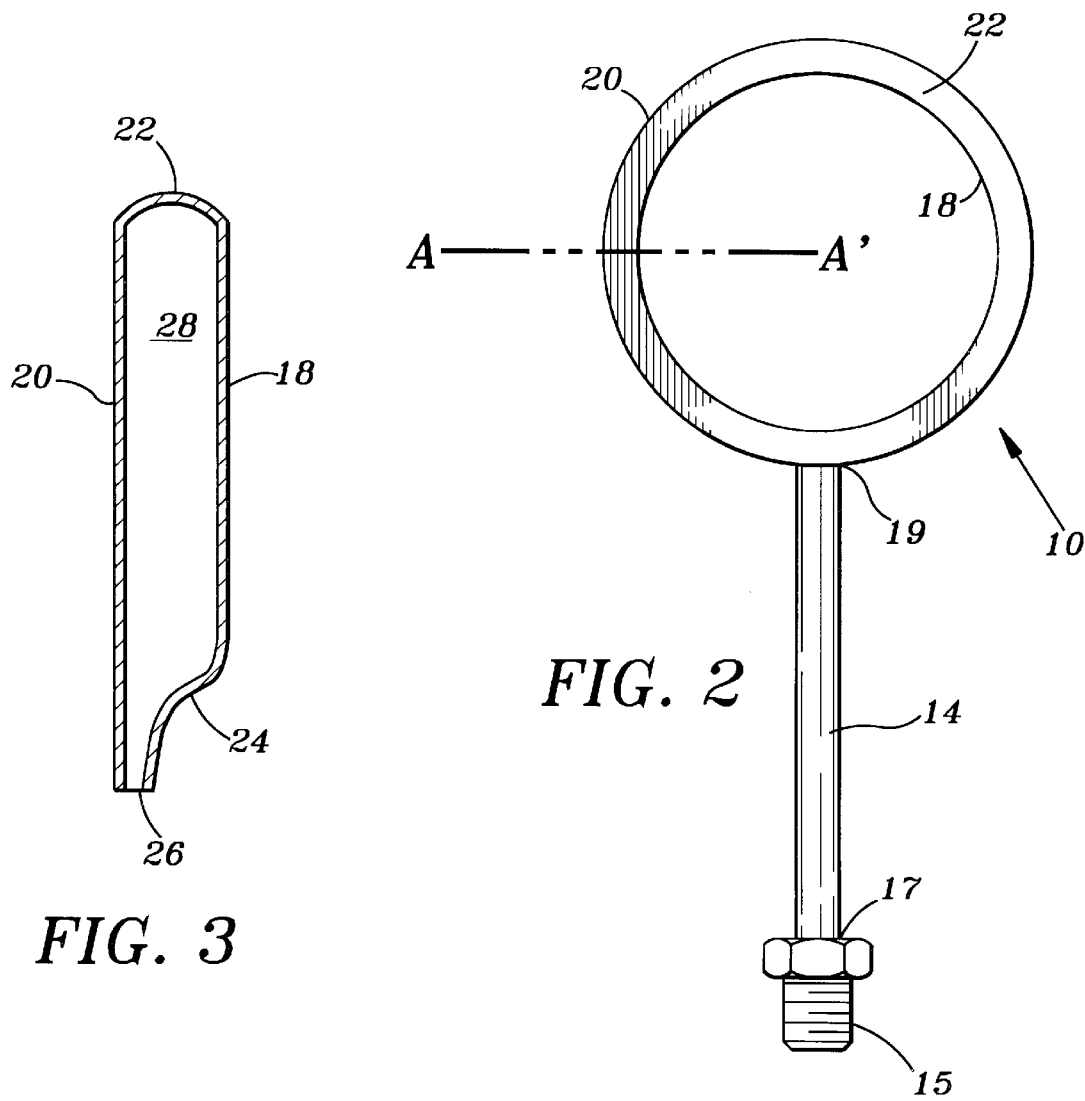
FIG. 3
FIG. 2

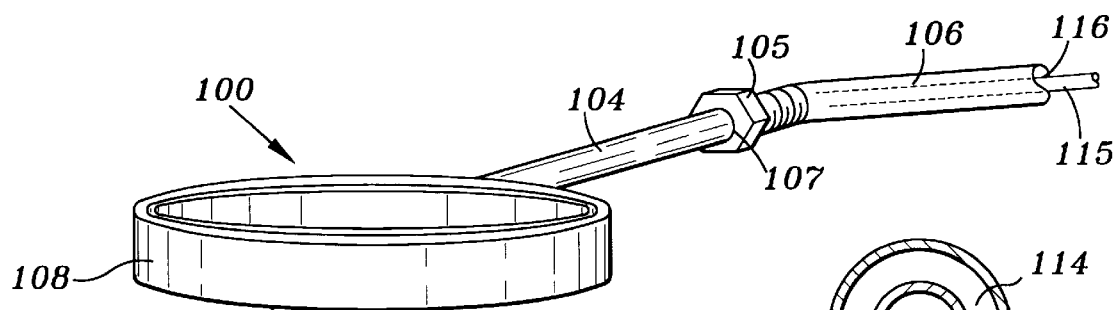
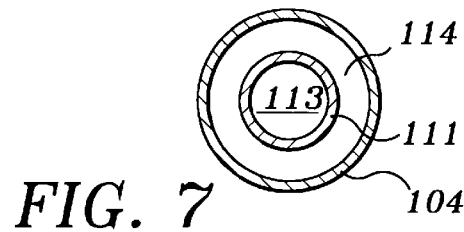
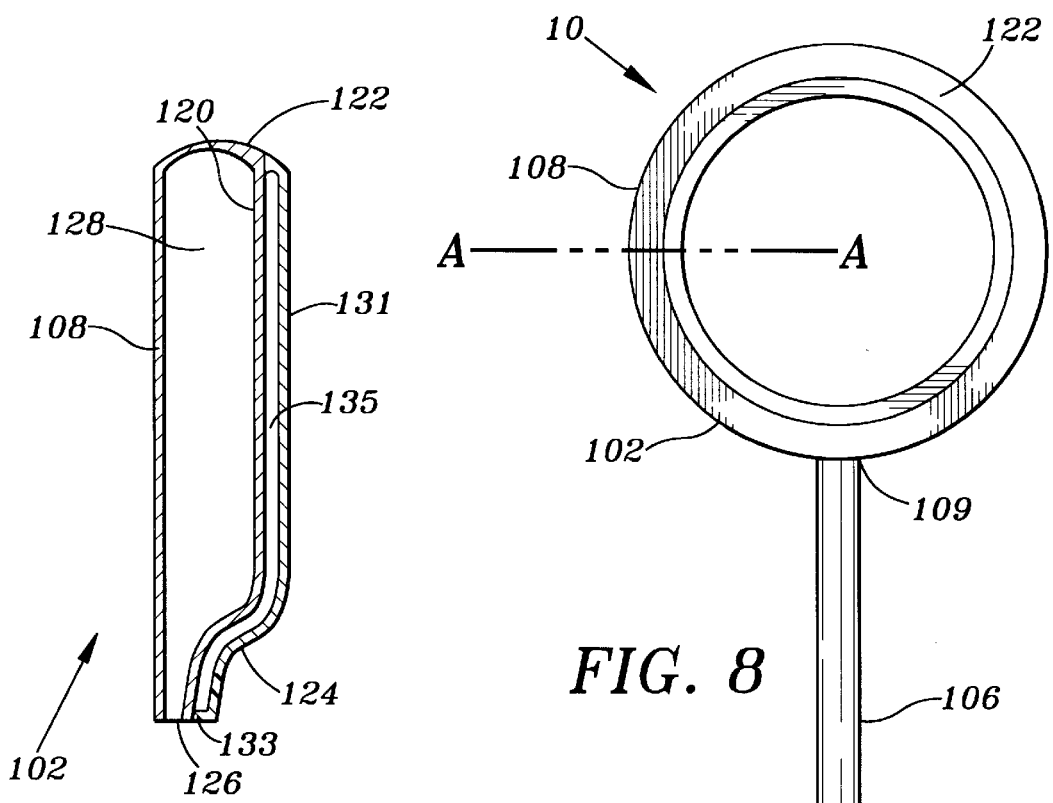
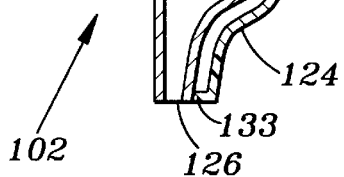
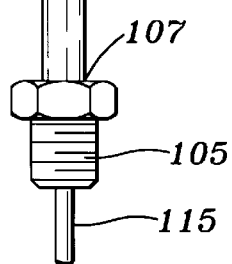

HYDRAULIC CAPSULORHEXITOME

TECHNICAL FIELD

This invention relates to surgical instruments, and more particularly to surgical instruments associated with intraocular lens implantation.

BACKGROUND OF THE INVENTION

Development of cataracts, a clouding of the material within the lens capsule of the eye, commonly accompanies the aging process. In response to this routine problem, eye surgeons have developed several techniques for cataract extraction. Generally, cataract extraction involves making an incision through the anterior surface of the lens capsule. Clouded material is removed through suction of the lens nucleus emulsion (phacoemulsification), without removing the entire lens capsule. After surgery, since a portion of the natural lens of the eye has been removed, light entering the eye through the cornea and pupil is unfocused. In order to correct this condition, an artificial intraocular lens is usually implanted directly into the eye after cataract extraction.

An essential step in cataract extraction is the incision of the anterior lens capsule. One current technique for incising the anterior lens capsule, known as capsulotomy, uses a straight intravenous needle with a sharp wedge attached to one end. The wedge is used manually or driven ultrasonically in a chopping motion to perforate the anterior capsule. This technique produces a hole with jagged edges, similar to the edges produced when one opens a can with a manual can opener.

Although this technique has been widely used in conjunction with cataract extractions, it is not entirely satisfactory. The geometry of an incision produced using capsulotomy is unpredictable and susceptible to linear tears. In the worst case, such tears in the capsule can result in the release of the lens nucleus into the vitreous cavity of the eye. Additionally, capsulotomy produces an irregular aperture in the anterior capsule, which may lead to asymmetrical scarring. This condition may allow the implanted intraocular lens to migrate out of the visual axis subsequent to surgery. Additionally, capsulotomy produces a large aperture which allows nuclear lens debris from phacoemulsification to impact the corneal endothelium. Normally, the corneal endothelium keeps the cornea optimally hydrated. Injury to this layer by impacted nuclear debris from phacoemulsification may lead to corneal edema and ultimately an irreversible clouding of the cornea.

SUMMARY OF THE INVENTION

The present invention comprises a novel surgical apparatus and method which overcomes the foregoing disadvantages associated with the prior art. The apparatus for capsulorhexis includes a hollow shaft, a hydraulic cutting member, and a conduit which connects the shaft to a source of high pressure fluid cutting medium. The high pressure fluid cutting medium flows through the conduit and hollow shaft to the hydraulic cutting member where it is directed through an annular jet to produce a smooth, continuous aperture in the anterior capsule of the eye.

The aperture is smaller and of a more controlled geometry than that produced by current techniques. This smaller aperture prevents nuclear lens debris from impacting the corneal endothelium and significantly reduces the likelihood of corneal edema and subsequent clouding.

Another advantage of the present invention is that the single cut produced by the apparatus for capsulorhexis promotes symmetrical scarring and implant fixation in the visual axis.

The apparatus and method for capsulorhexis of the present invention may be used to produce a small aperture in the anterior capsule. Other advantages and applications deriving from the use of the invention will readily suggest themselves to those skilled in the art.

DESCRIPTION OF THE DRAWINGS

A more complete understanding of the invention and the advantages thereof may be had by reference to the following Detailed Description when taken in conjunction with the accompanying Drawings wherein:

FIG. 1 is a perspective view of a first embodiment of the invention illustrating various features of the invention;

FIG. 2 is a top view of the first embodiment of the invention illustrating the general configuration of the cutting member;

FIG. 3 is a cross-sectional view of the cutting member of FIG. 2 taken along section A—A;

FIG. 6 is a perspective view of a second embodiment of the invention;

FIG. 7 is a cross sectional view of the hollow shaft of the apparatus of FIG. 6 taken along section B—B;

FIG. 8 is a top view of the second embodiment of the invention illustrating the general configuration of the cutting member; and FIG. 9 is a cross-sectional view of the cutting member of FIG. 8 taken along section A—A.

DETAILED DESCRIPTION OF THE INVENTION

Figure 4:
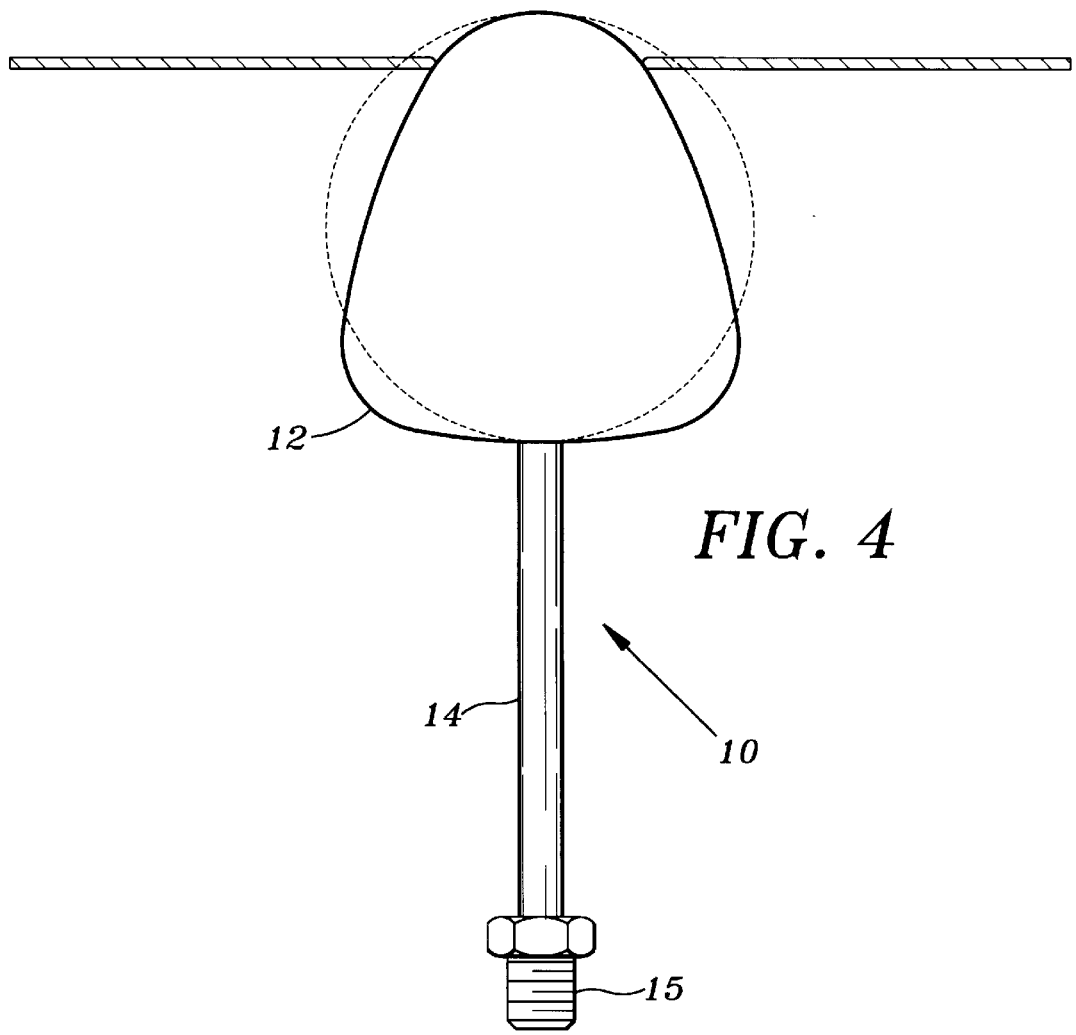
FIG. 4 is a top view of the apparatus of the present invention showing the deformation of the instrument as it enters the incision.

Referring now to the Drawings and in particular to FIGS. 1–3, there is shown an apparatus 10 for hydraulic capsulorhexis for incising a small circular aperture in the anterior capsule of the eye. The apparatus for capsulorhexis 10, or hydraulic capsulorhexitome, includes a cutting member 12, a hollow shaft 14, and a flexible conduit 16. The hollow shaft 14 defines a longitudinal channel 21 and is connected to the cutting member 12 at its distal end 19 and to a flexible conduit 16 at its proximate end 17 with connector 15. The flexible conduit 16 is connected to a pressurized source (not shown) of a substantially incompressible fluid such as a saline solution.

The cutting member 12 includes an annular channel 28 defined by an interior wall 18, an outer wall 20, and an upper wall 22. The annular channel 28 communicates with hollow shaft 14 for the flow of a generally incompressible fluid such as sterilized water or a saline solution through the longitudinal channel 21. A lower portion 24 of the interior wall 18 is curved or inclined outwardly toward the outer wall 20 to form a concentric nozzle-like orifice 26 that extends between the lower portion 24 of interior wall 18 and outer wall 20 around the circumference of the cutting member 12. Although as illustrated and described, the orifice 26 of cutting member 12 is continuous, it is contemplated that the orifice could be discontinuous, i.e., the inclined lower portion 24 of interior wall 18 could be connected to the outer wall 20 at intervals around the circumference of cutting member 12.

The cutting member 12 is preferably fabricated from a hard but flexible material such as a low carbon steel. Other metal alloys such as a titanium aluminum/vanadium or stainless steel alloy may be suitable along with other metallic alloys known to those skilled in the art. It is also contemplated that the cutting member 12 may be fabricated from a high strength polymer material such as mylar®.

Figure 5:
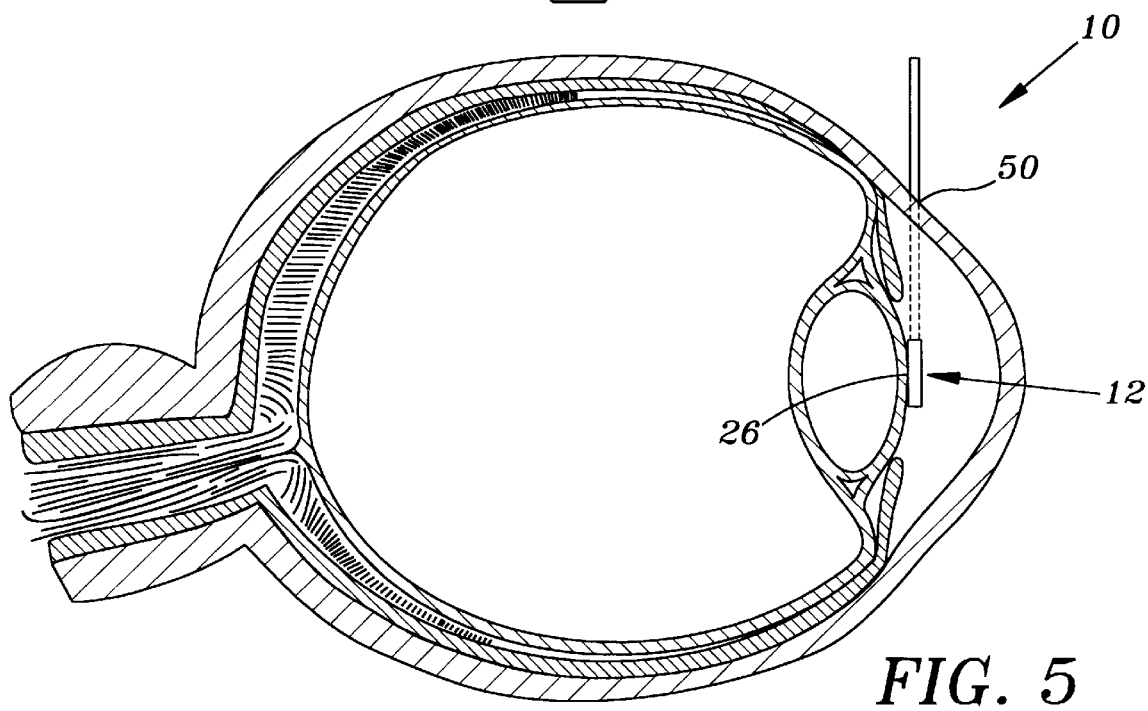
FIG. 5 is a cross-sectional side view of the eye illustrating the position of the apparatus relative to the eye during the initial stage of the capsulorhexis procedure.

As best illustrated in FIGS. 4 and 5, an initial small incision 50 is made in the eye where the cornea joins the sclera. The hydraulic capsulorhexitome 10 is inserted through the incision 50 and the cutting member 12 positioned inside the eye so that the concentric orifice 26 of the cutting member 12 is adjacent to the anterior capsule. As illustrated in FIG. 4, the cutting member 30 flexes and deforms as it is inserted into the incision.

However, once admitted through the incision 50, the cutting member 12 returns to its original form.

Referring now to FIG. 5 the orifice 26 is positioned substantially parallel to the plane of the eye next to the anterior capsule. After the hydraulic capsulorhexitome 10 is positioned, a stream of pressurized, substantially incompressible fluid is injected through conduit 16, hollow shaft 14 and annular channel 28 to produce a cutting action in a direction substantially normal to the plane of the eye. The pressurized fluid exits the cutting member 12 through concentric orifice 26 with sufficient velocity to produce a smooth, continuous, curvilinear aperture of predetermined geometry in the anterior capsule. The stream of incompressible fluid may be pulsed, for example ultrasonically. The aperture is significantly smaller than that produced by a capsulotomy. In addition, the aperture produced by the hydraulic capsulorhexitome 10 has a more controlled geometry than that produced by prior art surgical instruments. Subsequent to the incision of the anterior capsule the anterior capsule material is removed with a phacoemulsifier. Any attached fragments of anterior capsule tissue are excised and removed using a phacoemulsifier during this step.

Turning now to FIGS. 6 through 9, a second embodiment of the capsulorhexitome of the present invention is illustrated. Capsulorhexitome 100 includes a hollow shaft 104 connected to a cutting member 102 at its distal end 109 and to a flexible conduit 106 at its proximate end 107 with connector 105. As best illustrated by FIGS. 6 and 7, hollow shaft 104 includes an interior annular cylinder ill which defines an interior passageway 113 which communicates with an interior tube 115 that passes through flexible conduit 106. Hollow shaft 104 and interior annular cylinder 111 also define an exterior passageway 114 that communicates with the annular space 116 between flexible conduit 105 and interior tube 115.

Referring now to FIG. 8, cutting member 102 includes an annular channel 128 defined by an exterior wall 108, an intermediate wall 120, and an upper wall 122. The annular channel 128 communicates with exterior passageway 114 which in turn communicates with the annular space 116 between flexible conduit 105 and interior tube 115 for the flow of a substantially incompressible fluid such as a saline solution. A lower portion 124 of the intermediate wall 120 is curved or inclined toward the exterior wall 108 to form a concentric orifice 126 that extends between the lower portion 124 of intermediate wall 120 and exterior wall 108 around the circumference of the cutting member 102.

Cutting member 102 also includes an interior wall 131 and bottom wall 133 which with top wall 122, define a concentric interior pressurization chamber 135. Pressurization chamber 135 is positioned radially inside and adjacent to annular channel 128. Interior annular cylinder 111 communicates with interior tube 115 and interior pressurization chamber 135 for the flow of a pressurizing medium into pressurization chamber 135.

Cutting member 102 is preferably fabricated from a hard but flexible material such as a low carbon steel, a titanium aluminum/vanadium or stainless steel alloy or a high strength polymeric material. Due to the flexible nature of the materials from which cutting member 102 is fabricated, when a pressurized fluid is forced into interior channel 128 and through concentric orifice 126, there is a tendency for lower portion 124 of intermediate wall 120 to flex or bend away from external wall 108 due to the pressure of the fluid. If the lower portion 124 of intermediate wall 120 moves away from external wall 108 the movement increases the size of orifice 126. Such an increase in the size of orifice 126 may result in increased flow through the orifice 126 and an undesired reduction in pressure.

This tendency of lower portion 124 of intermediate wall 120 to flex when pressurized fluid is injected into interior channel 128 may be counteracted by pressurizing chamber 135 with a pressurizing medium which compensates for the forces applied by the pressurized fluid in interior channel 128. By pressurizing chamber 135 to the same or higher pressure than channel 128, the size of the orifice 126 may be controlled. Depending upon the materials of construction and the pressure applied to interior channel 128 it may, however, not be necessary to pressurize chamber 135 to the same or higher pressure as interior channel 128 and a lower pressure in chamber 135 may be sufficient to control the size of orifice 126.

As described above, the hydraulic capsulorhexitome 100 is positioned substantially parallel to the plane of the eye next to the anterior capsule. A pressurizing medium such as sterilized water is supplied to chamber 135 through interior tube 115 and interior annular cylinder 111 to control the size of orifice 126 when interior channel 128 is pressurized. A stream of pressurized, substantially incompressible fluid is supplied to annular space 116 from which the fluid flows through exterior passageway 114 to annular channel 128. The pressurized fluid exits the cutting member 102 through concentric orifice 126 with sufficient velocity to produce a smooth, continuous, curvilinear aperture of predetermined geometry in the anterior capsule.

The capsulorhexitome of the present invention produces a single cut and small aperture. This, in turn prevents debris from being deposited on the cornea during cataract extraction, and decreases the likelihood that a subsequently implanted lens will migrate, thereby overcoming many of the limitations and disadvantages of prior art devices used to incise the anterior lens capsule during cataract extraction.

Although the present invention has been illustrated in the accompanying Drawings and described in the foregoing Detailed Description, it will be appreciated by those skilled in the art that various modifications and rearrangements of the component parts and elements of the present invention are possible without departing from the spirit and scope of the invention. The following claims are intended to cover all such modifications that are within the scope of the invention.

We claim:

1. An apparatus for incising an aperture in the anterior capsule of the human eye comprising:
    a shaft having proximate and distal ends, said shaft defining a longitudinal channel for the flow of a substantially incompressible fluid from the proximate end to the distal end of said shaft;

a hydraulic cutter attached to said shaft at said distal end, comprising:
    an annular channel having an interior wall, an outer wall and an upper wall, said annular channel communicating with said longitudinal channel for the flow of a substantially incompressible fluid;
    a lower edge defining a portion of said cutter opposite the upper wall of the annular channel; and
    an annular orifice along the lower edge of said cutter, said annular orifice defined by a lower portion of said outer wall and a lower portion of said interior wall and communicating with said annular channel for hydraulic discharge of the substantially incompressible fluid from the annular orifice.

2. The apparatus of claim 1 wherein the cutter is circular.

3. An apparatus for incising an aperture in the anterior capsule of the human eye comprising:
    a shaft having proximate and distal ends, said shaft defining a longitudinal channel for the flow of a substantially incompressible fluid from the proximate end to the distal end of said shaft;
    a substantially circular cutter attached to said shaft at said distal end, said circular cutter defining an annular channel, said annular channel communicating with said longitudinal channel for the flow of a substantially incompressible fluid;
    said cutter further defining a substantially concentric orifice extending the length of said cutter, said substantially concentric orifice communicating with said annular channel for the flow of the substantially incompressible fluid from the annular channel; and
    an interior pressurization chamber for controlling the size of the orifice, said chamber positioned radially inward from and adjacent to said cutter, wherein pressure in said pressurization chamber exerts a radial force on the interior wall of the annular channel for controlling the size of the orifice.

4. The apparatus of claim 3 wherein the cutter comprises a flexible metallic material.

5. The apparatus of claim 4 wherein the flexible metallic material comprises a low carbon steel.

6. The apparatus of claim 4 wherein the flexible metallic material comprises a titanium aluminum/vanadium alloy.

7. The apparatus of claim 3 further comprising a conduit for supplying a pressurizing medium to the pressurization chamber.

8. The apparatus of claim 3 further comprising a source of pressurized, substantially incompressible fluid; and
    a coupling for connecting the proximate end of said shaft to the pressurized source of substantially incompressible fluid.

9. The apparatus of claim 3 wherein the source of pressurized, substantially incompressible fluid comprises a source of pressurized water.

10. An apparatus for incising an aperture in the anterior capsule of the human eye comprising:
    a shaft having proximate and distal ends, said shaft defining a longitudinal channel for the flow of a substantially incompressible fluid from the proximate end to the distal end of said shaft;
    a cutter of a flexible metallic material attached to said shaft at said distal end, said cutter defining an annular channel, said annular channel communicating with said longitudinal channel for the flow of a substantially incompressible fluid; and
    said cutter further defining an orifice extending the length of said cutter, said orifice communicating with said annular channel for the flow of the substantially incompressible fluid from the annular channel.

11. The apparatus of claim 10 wherein the flexible metallic material is a low carbon steel.

12. The apparatus of claim 10 wherein the flexible metallic material is a titanium aluminum/vanadium alloy.

13. An apparatus for incising an aperture in the anterior capsule of the human eye comprising:
    a shaft having proximate and distal ends, said shaft defining a longitudinal channel for the flow of a substantially incompressible fluid from the proximate end to the distal end of said shaft;
    a cutter attached to said shaft at said distal end, said cutter defining an annular channel, said annular channel communicating with said longitudinal channel for the flow of a substantially incompressible fluid;
    said cutter further defining an orifice extending the length of said cutter, said orifice communicating with said annular channel for the flow of the substantially incompressible fluid from the annular channel;
    a source of pressurized, substantially incompressible fluid; and
    a coupling for connecting the proximate end of said shaft to the pressurized source of substantially incompressible fluid.

14. The apparatus of claim 13 wherein the source of pressurized, substantially incompressible fluid comprises a source of pressured water.

15. An apparatus for incising an aperture in the anterior capsule of the human eye comprising;
    a shaft having proximate and distal ends, said shaft defining a longitudinal channel for the flow of a substantially incompressible fluid from the proximate end to the distal end of said shaft;
    a cutter attached to said shaft at said distal end, said cutter defining an annular channel, said annular channel communicating with said longitudinal channel for the flow of a substantially incompressible fluid;
    said cutter further defining an orifice extending the length of said cutter, said orifice communicating with said annular channel for the flow of the substantially incompressible fluid from the annular channel; and
    a concentric pressurization chamber for controlling the size of the orifice, said chamber positioned radially inward from and adjacent to said cutter, wherein pressure in the pressurization chamber exerts a radial force on the interior wall of the annular channel for controlling the size of the orifice.

16. A method for incising an apparatus in the anterior capsule of the human eye comprising the steps of:
    positioning a cutter with an orifice adjacent to the anterior capsule of the human eye; and
    injecting a pressurized substantially incompressible fluid through the orifice with sufficient velocity to cut an aperture of predetermined geometry in the anterior capsule.

17. The method of claim 16 wherein the step of injecting the substantially incompressible fluid includes producing a cutting action in a direction substantially normal to the plane of the eye.

18. The method of claim 16 wherein the substantially incompressible fluid is water.

19. The method of claim 16 wherein the substantially incompressible fluid is a saline solution.

20. The method of claim 16 further comprising the step of controlling the size of the orifice.

21. A method for incising an aperture in the anterior capsule of the human eye comprising the steps of:

positioning a cutter with a concentric orifice adjacent the anterior capsule of the human eye; and injecting a pressurized substantially incompressible fluid through the orifice at a velocity to produce a cutting action in a direction substantially normal to the plane of the eye.

* * * * *